(12) United States Patent
Christen et al.

(10) Patent No.: US 11,072,791 B2
(45) Date of Patent: Jul. 27, 2021

(54) PARALLEL FUNCTIONAL TESTING OF SYNTHETIC DNA PARTS, PATHWAYS, AND GENOMES

(71) Applicant: ETH Zurich, Zurich (CH)

(72) Inventors: Beat Christen, Baden (CH); Matthias Christen, Reinach BL (CH)

(73) Assignee: GIGABASES SWITZERLAND AG, Reinach BL (CH)

( * ) Notice: Subject to any disclaimer, the term of this patent is extended or adjusted under 35 U.S.C. 154(b) by 338 days.

(21) Appl. No.: 15/775,070

(22) PCT Filed: Nov. 18, 2016

(86) PCT No.: PCT/EP2016/078127
§ 371 (c)(1),
(2) Date: May 10, 2018

(87) PCT Pub. No.: WO2017/085249
PCT Pub. Date: May 26, 2017

(65) Prior Publication Data
US 2019/0032044 A1    Jan. 31, 2019

(30) Foreign Application Priority Data
Nov. 19, 2015 (EP) ..................... 15195390

(51) Int. Cl.
| | |
|---|---|
| *C12N 15/10* | (2006.01) |
| *C12Q 1/6809* | (2018.01) |
| *C12N 15/113* | (2010.01) |
| *C12N 15/70* | (2006.01) |

(52) U.S. Cl.
CPC ....... *C12N 15/1082* (2013.01); *C12N 15/102* (2013.01); *C12N 15/1093* (2013.01); *C12N 15/113* (2013.01); *C12N 15/70* (2013.01); *C12Q 1/6809* (2013.01)

(58) Field of Classification Search
None
See application file for complete search history.

(56) References Cited

U.S. PATENT DOCUMENTS

2013/0143745 A1    6/2013   Christen et al.

FOREIGN PATENT DOCUMENTS

| CN | 101270366 | 9/2008 |
|---|---|---|
| WO | 9915644 | 4/1999 |

OTHER PUBLICATIONS

Olsson et al., How important are post-translational modifications in p. 53 for selectivity in target-gene transcriptin and tumour suppression? 14 Cell Death and Differentiation 1561-575 (2007).*
B. Christen Et Al: "The essential genome of bacterium", Molecular Systems Biology, vol. 7, No. 1, 2011 Article 528 1-7.
Tim Van Opijnen Et Al: "Tn-seq: high-throughput parallel sequencing for fitness and genetic interaction studies in microorganisms", Nature Methods, vol. 6, No. 10, Oct. 1, 2009, pp. 767-772.
Mimi C. Yung et al: "Transposon Mutagenesis Paired with Deep Sequencing of Caulobacter crescentus under uranium stress reveals genes essential for detoxification and stress tolerance.", Journal of Bacteriology, vol. 197, No. 19, Oct. 1, 2015, pp. 3160-3172.

* cited by examiner

*Primary Examiner* — Nancy J Leith
(74) *Attorney, Agent, or Firm* — JMB Davis Ben-David (57) ABSTRACT

The invention relates to a process for determining the functionality of an artificial genetic element. An artificial genetic element designed to serve the same biological function as a native genetic element is introduced into cells, and the cells are subjected to conditions of high frequency transposon mutagenesis. Subsequently, a set of DNA sequences representative of a site of insertion of the transposable element is obtained from the cells and the frequency of insertion of the transposable element into the native genetic element and the artificial genetic element is determined. Comparing the frequency of transposon insertion allows for assigning a likelihood of functionality to said artificial functional element, which is high if the frequency of transposon insertion is essentially equal for both elements, and which is low if the frequency of transposon insertion is higher into the artificial genetic element.

11 Claims, 5 Drawing Sheets

Specification includes a Sequence Listing.

SEQUENCE LISTING

```
<160> NUMBER OF SEQ ID NOS: 1

<210> SEQ ID NO 1
<211> LENGTH: 15
<212> TYPE: DNA
<213> ORGANISM: Artificial Sequence
<220> FEATURE:
<223> OTHER INFORMATION: 15 bp long perfect match to the Tn5 transposon
      end sequence string

<400> SEQUENCE: 1
gtgtataaga gacag                                                    15
```

PARALLEL FUNCTIONAL TESTING OF SYNTHETIC DNA PARTS, PATHWAYS, AND GENOMES

CROSS-REFERENCE TO RELATED APPLICATIONS

This is the U.S. National Stage of International Patent Application No. PCT/EP2016/078127 filed on Nov. 18, 2016, which was published in English under PCT Article 21(2), and which in turn claims the priority of European Patent Application No. 15195390.8 filed Nov. 19, 2015.

SEQUENCE LISTING

The nucleic acid sequences provided herewith are shown using standard letter abbreviations for nucleotide bases as defined in 37 C.F.R. 1.822. Only one strand of each nucleic acid sequence is shown, but the complementary strand is understood as included by any reference to the displayed strand. The Sequence Listing is submitted as an ASCII text file named 95083_315_15 SEQ LISTING ST25, about 1 KB, created Oct. 15, 2018, which is incorporated by reference herein.

Synthetic Biology holds promise for solving challenging global problems. Of particular interest is the bio-systems design of pathways and entire microbial cells to produce food, fuels or compounds from renewable resources. Recently, large biosynthetic pathways and even synthetic copies of whole chromosomes have been successfully assembled. Despite these achievements, most large-scale synthesis efforts have maintained gene organisation and sequences from wild-type templates. However, the real potential of de novo synthesis resides in the engineering of completely refactored DNA molecules that lack biological counterparts.

A major challenge for synthetic biology is to navigate the design-build-test cycle in a more effective way. Today, error diagnosis and debugging of synthetic DNA modules is still very difficult and gets more arduous the more components a module encompasses. Our knowledge is limited on how genome-scale refactoring affects the functionality of DNA encoded instructions, simply because fast and cost-effective test methods to probe functionality of synthetic genome constructs are not available. Consequences of DNA refactoring on functionality are often non-obvious and difficult to predict. Because a single base substitution can either be neutral or completely disrupting the biological function encoded, it is difficult to tease apart which changes in DNA sequences are tolerated and which ones erase the genetic function encoded. Deciphering the encoded functionality of DNA (i.e. determining if a gene is capable of archiving its function within a cellular system) is far more challenging than DNA sequencing. As a result, we hesitate to alter the sequence and value sequence fidelity over functional fidelity.

The objective of the present invention is to provide means and methods to allow for massively parallel functional testing of synthetic DNA parts. This objective is attained by the subject matter of the independent claims.

The invention achieves leveraging the engineering of refactored bio-systems to the genomic scale, and assessing the part functionality of a synthetic genome design through a transposon-based circuit testing strategy (also referred to as Tncite in the following).

Through Tncite, the functionality of individual DNA encoded parts can be tested in parallel with base pair resolution. The method can be used for any genetic parts that i) confer core cellular functions or, ii) are conditionally essential or iii) of high-fitness relevance for a particular growth condition or environment or iv) encode for biological components such as biosynthetic pathway which end products are essential or can be genetically coupled to a positive selection marker.

Figure 1:
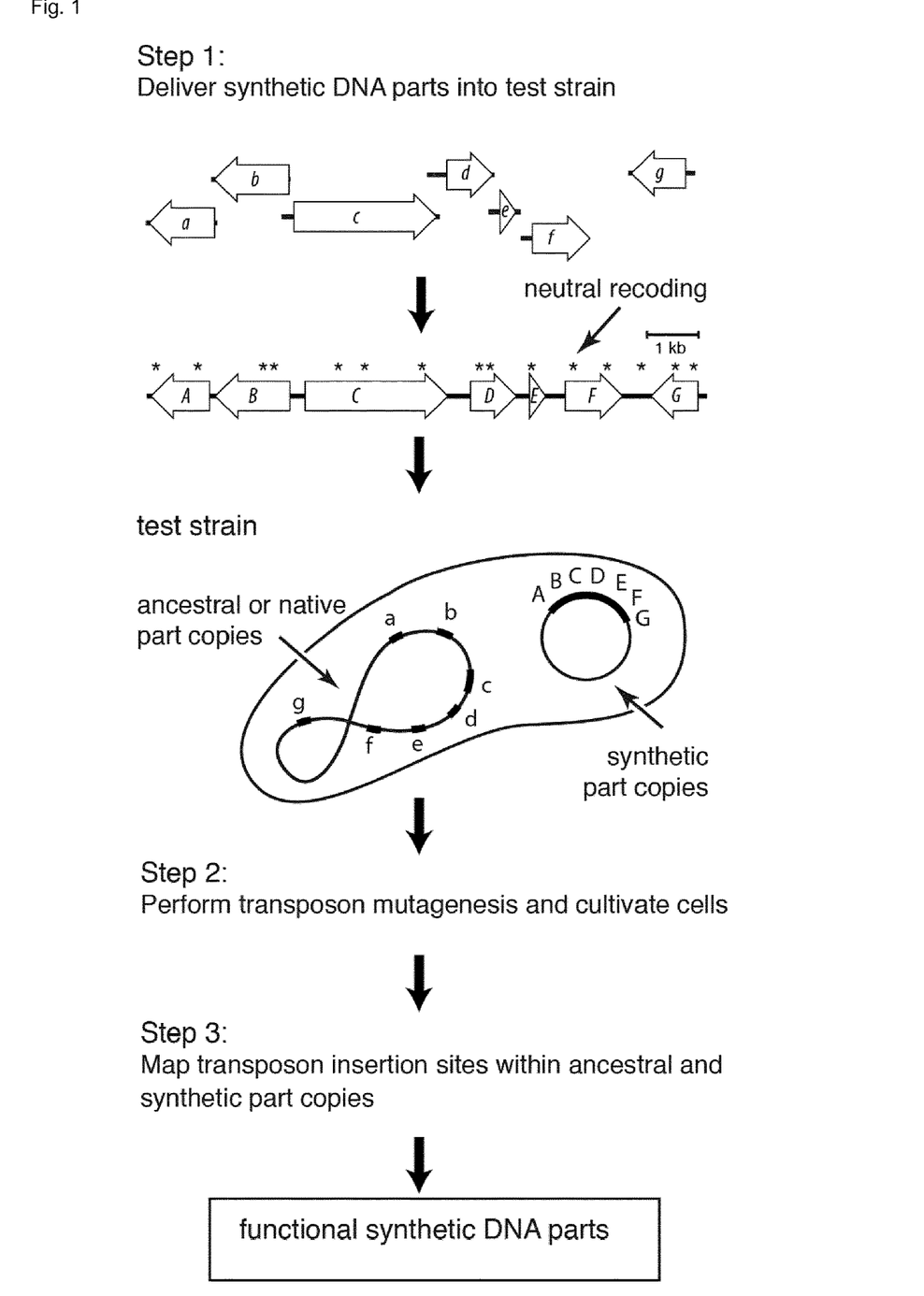
FIG. 1 shows the workflow of the Tncite part testing method

The Tncite part testing method is based on a three steps process (FIG. 1).

First Step: Synthetic DNA constructs (in size up to entire artificial genomes) encompassing essential or high-fitness gene functions (synthetic DNA part copies) are introduced into a cell that bears chromosomal or episomal copies of the equivalent gene functions (ancestral or native part copies). If synthetic and ancestral parts have similar sequences, neutral recoding or other base pair substitutions are used in the design process to introduce watermarks into the synthetic parts in order to unambiguously discriminate synthetic sequences from the corresponding ancestral parts sequences.

Second Step: Cells are subjected to high-throughput transposon mutagenesis, and cultivated under selective growth conditions.

Third Step: Tn (transposon) insertion sites are mapped within ancestral or synthetic part copies using high-throughput sequencing (transposon sequencing). The number of transposon insertions recovered for each part gives a precise measure for part functionality.

Figure 2:
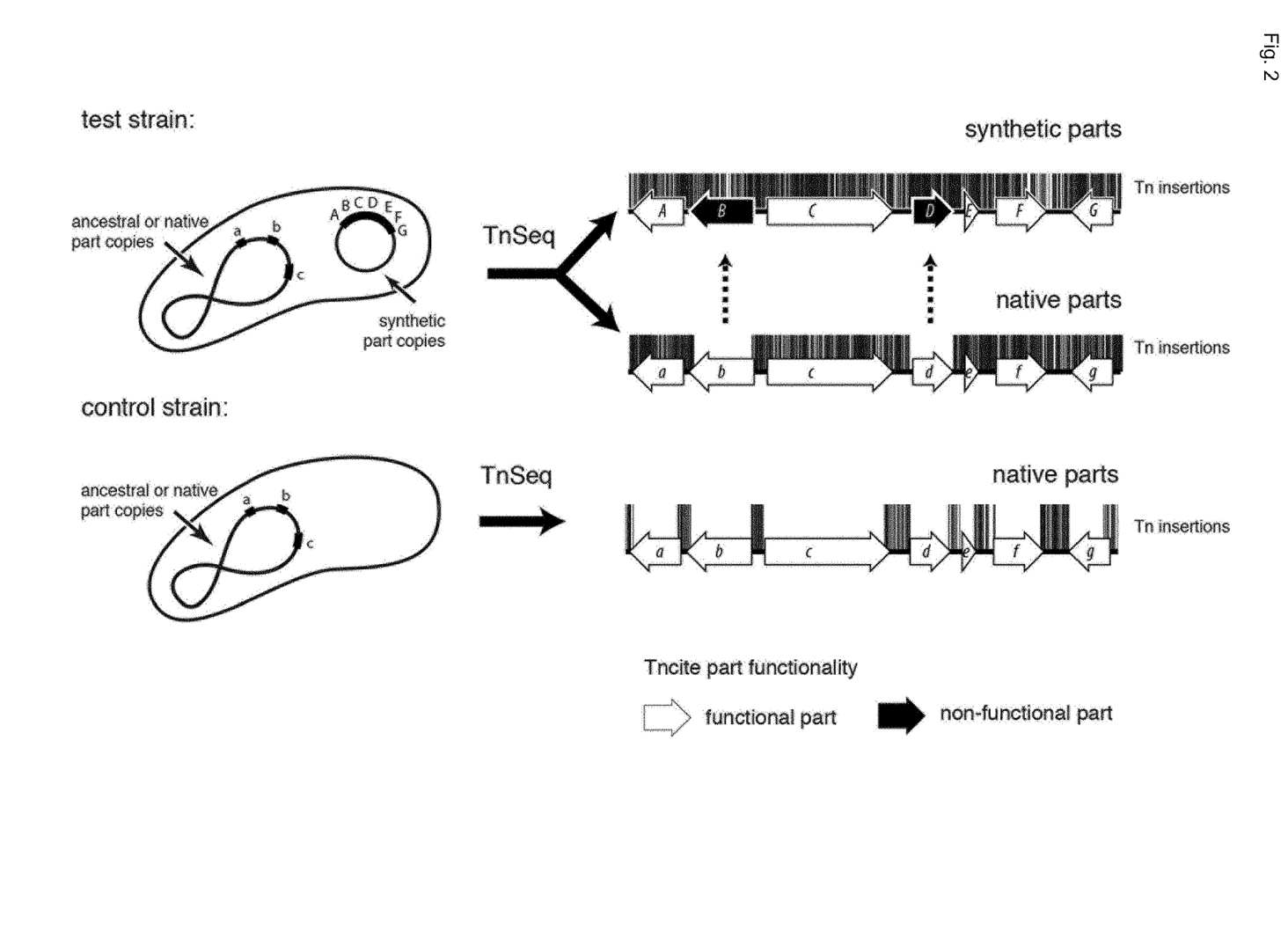
FIG. 2 shows the DNA part functionality analysis upon mapping of transposon insertion sites.

If the synthetic part is fully functional, equal transposon insertion frequencies are observed in both ancestral and corresponding synthetic part copies (FIG. 2). If the synthetic part is non-functional, the ancestral part copy contains no or only very few disruptive transposon insertions (because the ancestral part function will not be complemented by the synthetic part copy)(FIG. 2).

The Tncite method described herein does not depend on prior knowledge of sequence and functionality of the parts to be tested. In particular the method permits functional profiling of non-sequence verified synthetic DNA constructs as well as combinatorial part libraries composed of hundreds to thousands of genetic parts. This is due to the fact that sequences of the synthetic DNA constructs can be retrieved and reconstructed directly from the transposon sequencing data in addition to obtaining the part functionality information. This allows for effective and highly parallelised functionality testing of extensive genetic part libraries and multi-kilo base long synthetic DNA constructs encoding synthetic pathways or entire synthetic genomes. In sum, the invention is broadly applicable for synthetic biology to dramatically accelerate the design-engineer-test cycle in synthetic genome construction and bio-synthetic pathway engineering.

An aspect of the invention relates to a process for determining the functionality of an artificial genetic element, wherein the process comprises the steps of
 a) providing a first plurality of cells, wherein the cells comprise a native genetic element comprised within their genome;
 b) introducing an artificial genetic element expected or designed to serve the same biological function as said native genetic element into said plurality of cells, in a transgenesis step;
 c) subjecting said plurality of cells to conditions of high frequency transposon mutagenesis in a mutagenesis step, wherein a transposable element may be inserted at random into said native genetic element and/or said artificial genetic element, and thereafter d) obtaining a set of DNA sequences representative of a site of insertion of said transposable element (the transposon junction) from said plurality of cells in a sequencing step; and
e) determining the frequency of insertion of said transposable element into
    said native genetic element, resulting in a first frequency of transposon insertion, and
    said artificial genetic element, resulting in a second frequency of transposon insertion;
f) comparing the first frequency of transposon insertion into said native genetic element to the second frequency of transposon insertion into said artificial genetic element and
g) assigning a likelihood of functionality to said artificial functional element, which is
    high if the frequency of transposon insertion is essentially equal for both elements, and
    low if the frequency of transposon insertion is higher into the artificial genetic element.

In certain embodiments the cells used in the invention have a haploid genome prior to introduction of the artificial genetic elements. Introduction of the artificial genetic elements renders the cells merodiploid or —if the entire genome is added in artificial copy—diploid. The cells used in the invention are substantially indistinct on the genetic level. The native genetic element in some embodiments is essential to the propagation of the cells.

The sequence of the artificial genetic element and the sequence of the native genetic element can be distinguished, either by virtue of their fundamentally different sequence, or by virtue of certain sequence differences introduced deliberately in certain parts of the sequence that will allow distinguishing native and artificial sequences.

After the mutagenesis step, cells are propagated in order for any changes in fitness or viability to take effect. In many embodiments, overnight culture will suffice.

In certain embodiments, a fraction of said first plurality of cells, serving as control cells or the control strain (while the cells carrying an artificial element are labelled the test cells or test strain), is subjected to said mutagenesis step without having undergone said transgenesis step and a second set of DNA sequences representative of a site of insertion of said transposable element from said control cells is obtained, and a third frequency of insertion of said transposable element into said native genetic element of said control cells is determined, wherein
    i. if the first frequency of transposon insertion into of said native genetic element (of the test strain) is higher than the third frequency of transposon insertion (into the native genetic element of the control strain), the artificial functional element is assigned a high likelihood of being functional, and/or
    ii. if the first frequency of transposon insertion into of said native genetic element (of the test strain) is substantially equal to the third frequency of transposon insertion (into the native genetic element of the control strain), the artificial functional element is assigned a high likelihood of being non-functional.

In certain embodiments, said set of DNA sequences is obtained by isolating or identifying or sequencing transposon junction sequences. A transposon junction sequence comprises at least a part of the transposable element and at least a part of the native genetic element or said artificial element into which said transposable element has inserted. It may be isolated or identified or sequenced by a PCR. Methods include current PCR protocols for identification, sequencing or isolation of a DNA sequence known in the art and use
    a first primer capable of specifically annealing to a sequence comprised in said transposable element and a second primer capable of annealing to a sequence comprised in said native genetic element, or
    with said first primer, a second primer capable of annealing to said a sequence comprised in at least one part of said native genetic element and a third primer capable of annealing both to a sequence comprised in said artificial genetic element and to a sequence comprised in said native genetic element, or
    a third primer capable of annealing to a sequence comprised both in said artificial genetic element and to a sequence comprised in said native genetic element The skilled artisan understands that amplificates must be discernible by their sequence, i.e. sequence primers must be selected that are placed in such fashion as to allow such distinction, i.e. excluding primers that could lead to parts of the genetic element being exclusively amplified that are the same for both the artificial and the native genetic element.

In certain embodiments, the second primer and/or said third primer is a random primer or a semi-arbitrary primer comprising a 3'penta-nucleotide sequence or similar primers with defined short 3' sequences that are designed to anneal on said at least part of said native genetic element or said artificial genetic element.

Semi arbitrary primers and methods of their use are described in US2013/0143745, hereby incorporated by reference in its entirety.

In certain embodiments, the transposon mutagenesis is mediated by a genetic construct comprising said transposable element encoding a transposase operable in said cells. One example is a Tn5 transposase. In certain embodiments, the transposable element is under transcriptional control of a promotor operable in said cells.

In certain embodiments, the cells are selected from the group comprised of bacteria and archea, and haploid yeast strains.

In certain embodiments, the native genetic element is essential to propagation of said cells.

In certain embodiments, a plurality of artificial genetic elements is introduced into said plurality of cells, wherein each of said plurality of artificial genetic elements is distinct from any other one of said plurality of artificial genetic elements and serves a different function, and said plurality of cells comprise a plurality of native genetic elements corresponding in function to said plurality of artificial genetic elements. Each artificial element has a corresponding native element that is essential for the cell or has a high contribution to its fitness.

In certain embodiments, the plurality of artificial genetic elements is introduced into said plurality of cells comprised within the same nucleic acid molecule, i.e. as part of a construct comprising more than one, often many, artificial elements.

In certain embodiments, the nucleic acid molecule is a plasmid or an artificial chromosome.

In certain embodiments, the set of DNA sequences comprises more than (>) 1.000 sequences, particularly >10.000 sequences.

In certain embodiments, the artificial genetic element is selected from the group comprised of a promoter, an operator or other transcriptional control elements, ribosomal binding sites or other translational regulatory sequences, an open reading frame, an operon, a tRNA, a ribosomal or other RNA gene and a transcription terminator.

Using hyper-saturated transposon mutagenesis coupled to high throughput sequencing (Tnseq), the inventors recently identified the entire set of essential sequences of the cell-cycle model organism *Caulobacter crescentus*. Out of these sequences, the inventors have compiled a synthetic genome encoding the most fundamental functions of a bacterial cell. The genome design implements strong sequence refactoring, part restructuring and complete recoding of all CDSs.

Figure 4:
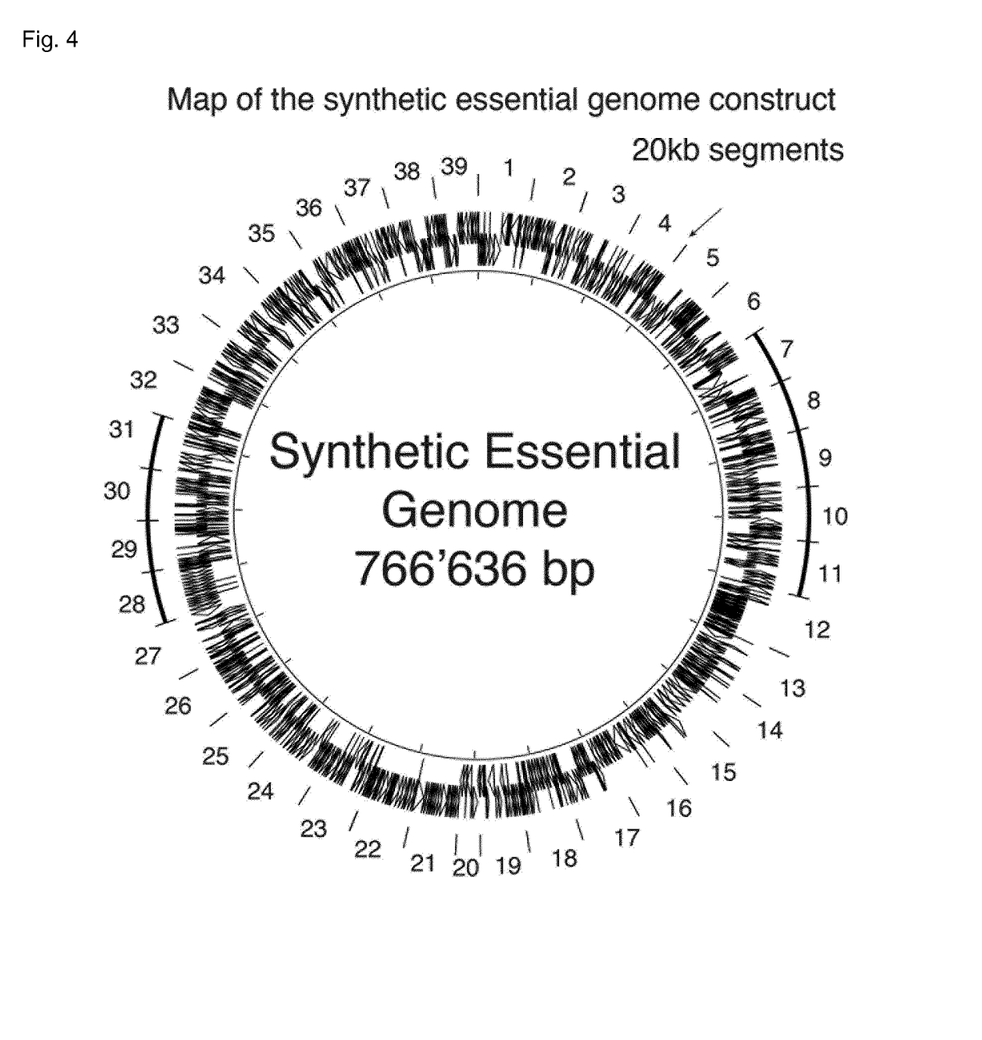
FIG. 4 shows the circular map of the essential synthetic genome segments tested by Tncite
Figure 5:
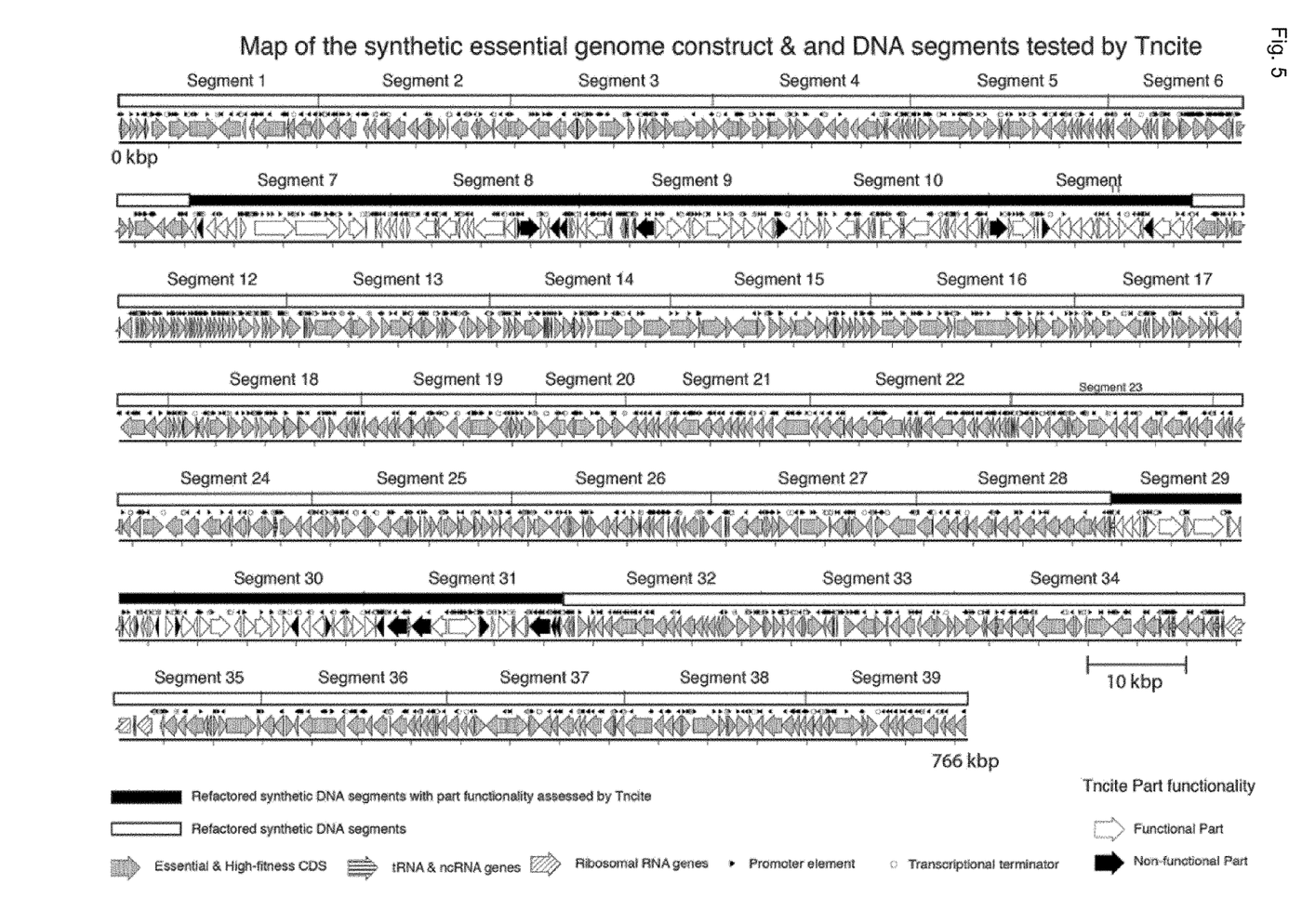
FIG. 5 shows a linear map of the essential synthetic genome segments tested by Tncite Tab 1-9 show functionality assessment of the eight 20 kb synthetic test segments.

Certain embodiments of the present invention take the following steps: A) Synthesis of twenty approx. 20 kb long synthetic segments composed of 30-40 refactored DNA parts is performed. B) Segments are plasmid-cloned and shuttled into a suitable host cell, e.g. *Caulobacter*, to produce merodiploid test-strains. Hence, for each refactored DNA part on the plasmid a synonymous copy exists on the chromosome. C) Test strains are then subjected to hyper-saturated transposon mutagenesis coupled to high throughput sequencing (Tnseq). D) To assess part functionality, a determination is performed as to whether disruptive transposon insertions occur within formerly essential chromosome sequences. Such events only occur if the refactored parts on the plasmid are fully functional and compensate for the loss of the chromosomal parts. In a prove of concept study the inventors have verified proper part functioning for 108 (out of 136 assayed) refactored DNA parts corresponding to 20% of a synthetic genome design (FIGS. 4 and 5 and Tables 1-8).

The 136 functionally verified DNA parts have been sequence optimized for de novo DNA synthesis and completely sequence tamed by recoding using the Genome Calligrapher Software algorithm. The Genome Calligrapher Software algorithm for DNA refactoring, codon optimization and methods of their use are described in (Christen et al. ACS Synthetic Biology 2015 DOI: 10.1021/acssynbio.5b00087), hereby incorporated by reference in its entirety.

Figure 3:
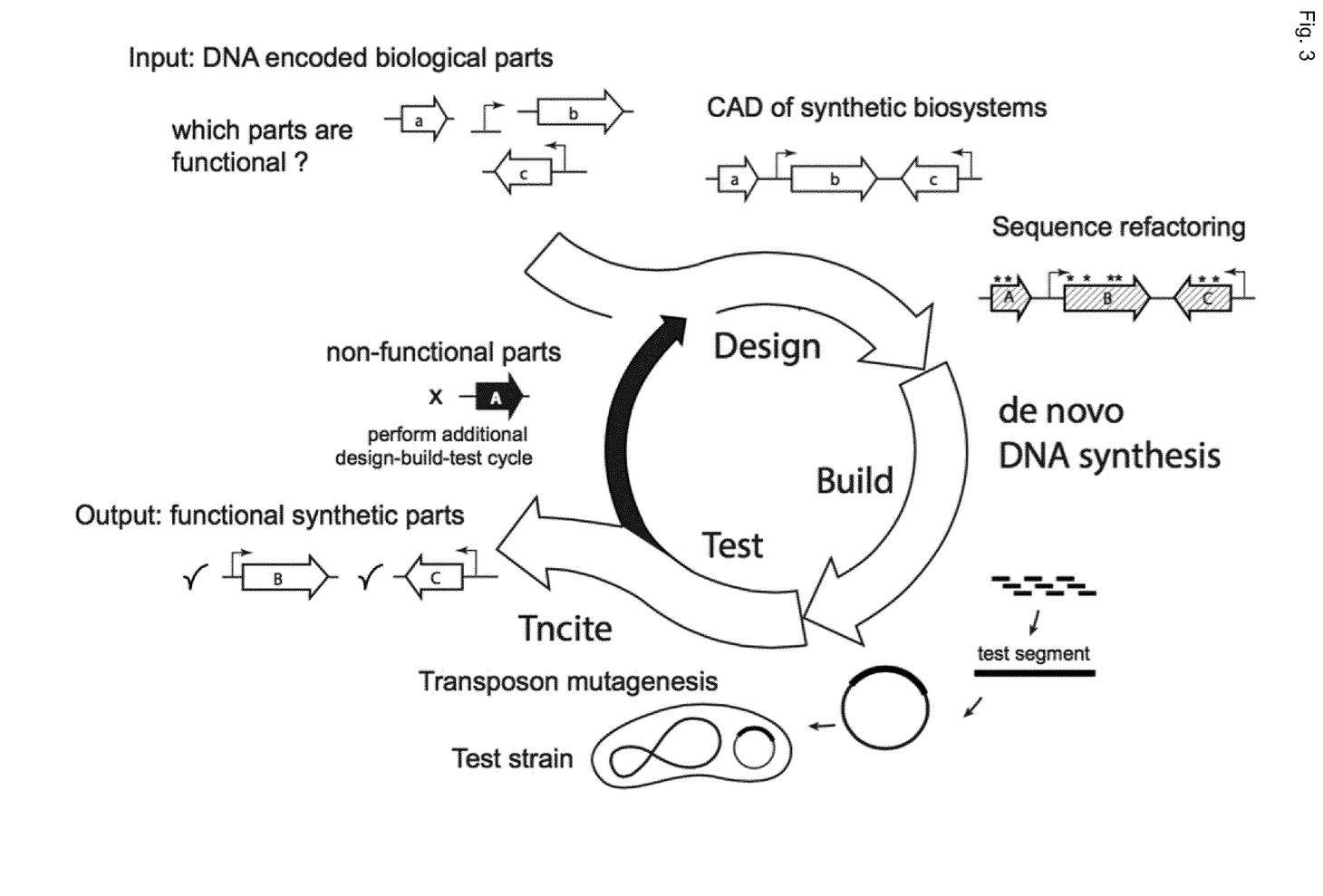
FIG. 3 shows the implementation of Tncite into the design-build-test cycle of synthetic biology.

The 108 functional DNA parts can be modularly assembled into complex bio-systems ranging from pathways to streamlined platform organisms with fully defined genetic makeups. In addition the 28 non-functional synthetic parts diagnosed can be redesigned in additional design-build-test cycles to improve functionality (FIG. 3). Understanding why certain parts are non-functional will lead towards improved biological rules for synthetic DNA design and will reveal critical gaps in our understanding how genomes program biological functions.

The Tncite approach for genome-scale synthetic part testing offers new opportunities to expand the sequence design space for biological systems engineering. As a result, research in synthetic biology and synthetic genomics will no longer be restricted to construct designs based on existing DNA sequences. With testing strategies in place to probe the functionality of large-scale DNA sequence, it will become feasible to radically change sequences without affecting the underlying biological functions. On one hand, this will have fare reaching consequences on how fast functional synthetic genome designs can be accomplished. In addition greater sequence flexibility enables more dramatic sequence refactoring, including sequence optimization for de novo DNA synthesis, codon usage adaptations, genetic code editing, and recoding of CDSs to erase overlapping gene regulatory features that cause interference between DNA parts and or host cells. Furthermore, de-fragmentation for grouping together related genetic functions to facilitate co-regulation and exchange becomes feasible (for example grouping together tRNAs or genes involved in lipid metabolism, genome replication and stability, etc.).

Wherever alternatives for single separable features are laid out herein as "embodiments", it is to be understood that such alternatives may be combined freely to form discrete embodiments of the invention disclosed herein.

The invention is further illustrated by the following examples and figures, from which further embodiments and advantages can be drawn. These examples are meant to illustrate the invention but not to limit its scope.

EXAMPLES

Material and Methods:

Design of a Synthetic Essential Genome Construct.

The comprehensive list of DNA sequences (DNA parts) encoding essential and high-fitness functions required for rich-media growth of *Caulobacter crescentus* was generated using a previously identified essential genome data set (Christen et al. 2011, J. Mol. Syst. Biol.). The DNA part list includes DNA sequences encoding proteins, RNA and regulatory features as well as small essential inter-genic sequences. Part boundaries of protein coding genes were set to the CDS coordinates according to the *Caulobacter crescentus* NA1000 genome annotation (NCBI Accession: NC_011916.1) plus additional 5' regulatory sequences (promoters) and terminator regions. Boundaries of regulatory upstream sequences of essential genes were set according to previously identified essential promoter regions (Christen et al. 2011, *Molecular Systems Biology* 2011; 7 (1): 52) and, when necessary, were enlarged to include strong transcriptional start sites as determined by RNAseq. For essential or high-fitness genes, predicted Rho-independent terminator sequences were included. Essential and high-fitness DNA parts were concatenated in order and orientation as found on the wild-type genome and compiled into a 766828 base pair long synthetic genome constructs. This genome construct was then partitioned into thirty-nine 20 kb long segments (FIGS. 4 and 5) that were further partitioned into 3-4 kb DNA building blocks.

Sequence Optimization and Synthesis of Eight 20 kb Synthetic Genome Segments.

To optimize the sequence of the eight 20 kb synthetic genome segments (segment 7, 8, 9, 10, 11 and segment 29, 30 and 31, for an overview of the segments, see FIGS. 4 and 5) protein coding sequences were refactored by neutral recoding (synonymous codon replacement) to erase disallowed sequence patterns known to inhibit large-scale de novo DNA synthesis. The recoding probability across different segments was gradually incremented from 0.125 to 1.0. The first four amino acids codons of protein coding sequences (CDS) were excluded from recoding to maintain potential translational and other regulatory signals. Disallowed sequences removed upon recoding included endonuclease sites for BsaI, AarI, BspQI, PacI and PmeI. Furthermore, the AGT, ATA, AGA, GTA and AGG codons, which are rare codons in *Caulobacter crescentus*, were set as immutable codons (neither replaced or introduced upon recoding). The amber stop codons TAG and the two TTA and TTG codon for leucine were erased upon recoding. The eight 20 kb long synthetic essential genome segments were partitioned and ordered as synthetic dsDNA building blocks from a commercial provider of de novo DNA synthesis (Gen9, Inc. Cambridge, Mass., USA). The 3 kb synthetic dsDNA building blocks were subsequently assembled into 20 kb segments and cloned into the low copy plasmid pMR10 (GenBank accession: JJ606312.1) using yeast recombineering. The assembled 20 kb synthetic segment were sequence verified using PacBio sequencing.

Construction of Mero-Diploid Test Strains and Transposon Mutagenesis.

Sequence verified pMR10 plasmid harboring the different 20 kb long synthetic DNA segments of the essential genome design were conjugated from *E. coli* S17-1 into wild-type *Caulobacter crescentus* NA1000 to produce a set of 8 mero-diploid test strains. To generate hyper saturated transposon libraries, a conjugation based mutagenesis procedure was used as previously described (Christen et al. 2010, *Proc Natl Acad Sci USA,* 2010; 107 (10): 4681-86). In brief, a Tn5 transposon derivative bearing transposon internal barcode sequences was conjugated from an *E. coli* S17-1 donor strain into the mero-diploid *Caulobacter crescentus* test strain bearing the different 20 kb long synthetic DNA segments on pMR10 plasmids. In addition, a control strain bearing only the empty pMR10 plasmid was also subjected to Tn5 mutagenesis. To multiplex Tncite experiments, Tn5 transposon with distinct 4 base long internal barcode sequences were used for mutagenesis of the different test strains. After overnight incubation on peptone yeast plates (PYE) supplemented with xylose, cells from each mating filter were harvested, resuspended in 800 µl PYE and 100 µl aliquots were plated onto PYE plates containing gentamycin, nalidixic acid, kanamycin and xylose. Plates were incubated for three days at 30° C. and transposon mutant libraries from each plate were pooled.

Parallel Amplification of Transposon Junctions by Semi-Arbitrary PCR.

Amplification of transposon junctions carrying terminal adapters compatible with illumina sequencing was performed as previously described (Christen et al. 2011, J. Mol. Syst. Biol.). For the first and second round of PCR, Taq polymerase mix (BioMix Red, Bioline, USA) was used. PCR amplification was carried out in 10 µl reaction volumes in 384 well PCR plates on a thermocycler instrument (C1000 touch, BioRad, Cressier, Switzerland). For the first round of PCR the M13 primer was used in conjunction with arbitrary PCR primers as previously described (Christen et al. 2011, *Molecular Systems Biology* 2011; 7 (1): 52). The first PCR amplification was performed according to following PCR program: (1) 94° C. for 3 min, (2) 94° C. for 30 s, (3) 42° C. for 30 s, slope −1° C./cycle, (4) 72° C. for 1 min, (5) go to step 2, 6 times, (6) 94° C. for 30 s, (7) 58° C. for 30 s, (8) 72° C. for 1 min, (9) go to step 6, 25 times, (10) 72° C. for 3 min, (11) 12° C. hold. Product of first round of PCR was further amplified in a second nested PCR step using the Illumina paired-end primers #128 and #129 and 1 µl of the first round PCR product as template. Amplification was performed according to following thermocycling conditions: (1) 94° C. for 3 min, (2) 94° C. for 30 s, (3) 64° C. for 30 s, (4) 72° C. for 1 min, (5) go to step 2, 30 times, (6) 72° C. for 3 min, (7) 12° C. hold.

DNA Library Purification and Illumina Sequencing.

PCR products from each Tncite experiment were combined and DNA libraries were size selected by electrophoresis on a 2% agarose gel. DNA fragments between 200 bp and 700 bp were isolated and purified over column (Macherey-Nagel, Switzerland). The DNA concentration of each sample was quantified on a Nanodrop spectrometer (Nanodrop, Wilmington, Del., USA) and samples from different mutant libraries were combined. Next-generation sequencing and cluster-generation was performed within standard Illumina paired-end flow-cells (Illumina HiSeq chemistry v4) and settings according to the Illumina HiSeq cluster kit v4 protocol. The DNA samples were titrated to produce approximately $2*10^8$ clusters per HiSeq flow cell lane. DNA samples were paired-end sequenced with 125 bases from both ends on a HiSeq illumina instrument using illumina sequencing chemistry version v4 and sequencing primers PE1.0 and PE2.0. Standard base-calling from raw images was performed according to the genome analyzer software suite OLB (Illumine). A phiX reference spike-in was used to calculate crosstalk matrixes and calibrate phasing parameters. Sequencing was performed at the Functional Genomics Center Zürich.

Sequence Analysis and Mapping of Transposon Insertion Sites.

Raw read processing, sequence alignment and genomic insertion site analysis was performed using a custom sequence analysis pipeline based on Python, Biopython, bwa, and Matlab routines. Low quality reads as identified by a low phred score were discarded. Transposon reads with a 15 bp long perfect match to the Tn5 transposon end sequence string ['GTGTATAAGAGACAG'] were selected. The first read of paired end sequences was trimmed to remove the transposon end sequence. Mate reads were trimmed to remove 5' sequences corresponding to the arbitrary PCR primer. Demultiplexing into the different Tncite experiments was performed according to the 4 bp long internal transposon barcode sequences adjacent to the transposon end. Adapter sequences corresponding to the illumina PE.2.0 adapter and the arbitrary PCR primer sequences were trimmed from the 3' end of the first read of each paired end read pair. Similarly, the reverse complement of the Tn5 transposon end sequence was trimmed from the 3' end of the second read. Adapter sequences were detected using Python string comparison with a 15 bp search window. The genomic insert size from each paired end read was inferred by testing for overlapping read end sequences between read 1 and read 2 sequences. Only read pairs with genomic inserts larger than 15 base pairs were selected. Reads were aligned with bwa-07.12 (Li and Durbin, 2009, *Bioinformatics*. 2009 Jul. 15; 25(14):1754-60) onto the *Caulobacter crescentus* NA1000 reference genome NC_011916 and the corresponding sequences of the plasmids bearing 20 kb long synthetic DNA cassettes. Reads with proper paired-end alignment and no mismatches within the first 15 bp of each read end were retrieved. Unique mapping positions with at least one of the paired end reads unambiguously mapped to a genome and with insert size smaller than 500 bases were considered for subsequent analysis. Upon insertion into the target DNA, Tn5 transposition generates a nine base pair long duplication, which was taken into account for subsequent insertion site analysis. The location of a given transposon insertion was defined as the genome position of the first reference base detected immediately after reading out of the transposon I-end, which contains an outward pointing Pxyl promoter (Christen et al. 2011, J. Mol. Syst. Biol., ibid.). A custom Matlab script was used to analyze global insertion statistics and calculate transposon insertion occurrence and distributions within each annotated GenBank feature of the *Caulobacter crescentus* NA1000 genome and corresponding plasmids. The output of the Matlab analysis consists of an insertion matric listing for each GenBank feature the total number of transposon insertions recovered and additional information about the distribution, orientation and reading frame of transposon insertions. Metrics and routines applied for this analysis have been previously described (Christen et al. 2011, J. Mol. Syst. Biol. Ibid.).

Parallel Functionality Analysis of Synthetic DNA Parts.

Transposon insertion numbers are normalized to account for differences in the global number of transposon insertion sites mapped between the different samples. For each test-strain, the numbers of unique transposon insertions within synthetic DNA parts and ancestral (native) part copies were determined. In addition, the numbers of transposon insertions within ancestral part copies were determined for a control strain that bears only the empty pMR10 plasmid. Synthetic parts were classified according to following rule. If a given synthetic DNA parts displays a significant level of insertions but the corresponding ancestral part harbours only very few insertions, the synthetic part is classified as non-functional. If both the synthetic and ancestral parts show roughly similar numbers of transposon insertions and/or the ancestral part of the control strain shows significantly lower numbers of insertions, the synthetic DNA part is classified as functional (Table 1 to 9). Relative fitness values for each DNA part is defined by the ratio between observed and expected transposon insertions hits assuming random transposition events and neutral fitness costs along the genome. The difference in fitness values between the ancestral part of the mero-diploid test strain and a control strain is used to quantify the level of functionality of a synthetic DNA part. Examples of fitness values assigned based on Tncite analysis are shown in Tables 1-9, which gives Tncite Part Functionality Assessment of different segments of a *Caulobacter crescentus* Synthetic Genome.

The table headers have the following meaning:

Name: Locus name of the synthetic DNA part

[bp]: Length of the synthetic DNA part's coding sequence in base pairs

CON: Control strain=*C. crescentus* NA1000 wild type under PYE rich media condition TEST: Synthetic test strain *C. crescentus* NA1000 with pMR10 plasmid containing a 20.6 kb (Segment 7a, 7b), 19.3 kb (Segment 8), 21.4 kb (Segment 9), 20.4 kb (Segment 10), 20.8 kb (Segment 11), 19.0 kb (Segment 29), 19.4 kb (Segment 30) and 20.2 kb (Segment 31) long synthetic DNA segment with essential and high-fitness genetic parts subjected to Tncite functionality analysis.

FUNCT: Tn cite functionality (non-funct.: non-functional)

The relative fitness values for each DNA part is defined by the ratio between observed and expected transposon insertions hits assuming random transposition events and neutral fitness costs.

TABLE 1

Segment 7a

| Name | Product | [bp] | Tn5 Hits CON | Tn5 Hits TEST | Fitness Value CON | Fitness Value TEST | FUNCT |
|---|---|---|---|---|---|---|---|
| CSYN00517 | peptidyl-tRNA hydrolase | 617 | 8 | 54 | 0.11 | 1.42 | functional |
| CSYN00518 | LSU ribosomal protein L25P | 593 | 31 | 18 | 0.45 | 0.49 | non-functional |
| CSYN00520 | ribose-phosphate pyrophosphokinase | 938 | 0 | 0 | 0 | 0 | non-functional |
| CSYN00524 | conserved hypothetical cytosolic protein | 1124 | 15 | 140 | 0.12 | 2.01 | functional |
| CSYN00525 | prolipoprotein diacylglyceryl transferase | 908 | 17 | 69 | 0.16 | 1.23 | functional |
| CSYN00530 | LSU ribosomal protein L10P | 518 | 0 | 18 | 0 | 0.56 | functional |
| CSYN00531 | LSU ribosomal protein L12P (L7/L12) | 383 | 0 | 6 | 0 | 0.25 | functional |
| CSYN00536 | DNA-directed RNA polymerase beta chain | 4070 | 3 | 224 | 0.01 | 0.89 | functional |
| CSYN00537 | DNA-directed RNA polymerase beta chain | 4190 | 7 | 211 | 0.01 | 0.81 | functional |
| CSYN00546 | conserved hypothetical protein | 782 | 0 | 48 | 0 | 0.99 | functional |
| CSYN00564 | sensory transduction protein kinase CenK | 1505 | 2 | 96 | 0.01 | 1.03 | functional |
| CSYN00678 | LSU ribosomal protein L11P | 431 | 3 | 8 | 0.06 | 0.3 | functional |
| CSYN00684 | ChrR-family | 638 | 11 | 13 | 0.15 | 0.33 | functional |

Segment-7a contains a set of 13 recoded genes that are essential or of high-fitness cost for standard growth in PYE media. Two synthetic parts out of 13 (15.4%) are non-functional. Proper part functioning is verified for the remaining 11 genes representing 84.6% of the synthetic parts located on segment-7a. A total of 345,628 transposon insertions were mapped for the test strain segment-7a.

TABLE 2

Segment 7b

| Name | Product | [bp] | Tn5 Hits CON | Tn5 Hits TEST | Fitness Value CON | Fitness Value TEST | FUNCT |
|---|---|---|---|---|---|---|---|
| CSYN00517 | peptidyl-tRNA hydrolase | 617 | 8 | 45 | 0.11 | 1.27 | functional |
| CSYN00518 | LSU ribosomal protein L25P | 593 | 31 | 20 | 0.45 | 0.59 | non-functional |
| CSYN00520 | ribose-phosphate pyrophosphokinase | 938 | 0 | 63 | 0 | 1.16 | functional |
| CSYN00524 | conserved hypothetical cytosolic protein | 1124 | 15 | 89 | 0.12 | 1.37 | functional |
| CSYN00525 | prolipoprotein diacylglyceryl transferase | 908 | 17 | 44 | 0.16 | 0.84 | functional |
| CSYN00530 | LSU ribosomal protein L10P | 518 | 0 | 11 | 0 | 0.37 | functional |
| CSYN00531 | LSU ribosomal protein L12P (L7/L12) | 383 | 0 | 12 | 0 | 0.54 | functional |
| CSYN00536 | DNA-directed RNA polymerase beta chain | 4070 | 3 | 332 | 0.01 | 1.41 | functional |
| CSYN00537 | DNA-directed RNA polymerase beta chain | 4190 | 7 | 145 | 0.01 | 0.6 | functional |
| CSYN00546 | conserved hypothetical protein | 782 | 0 | 32 | 0 | 0.71 | functional |
| CSYN00564 | sensory transduction protein kinase CenK | 1505 | 2 | 65 | 0.01 | 0.75 | functional |
| CSYN00678 | LSU ribosomal protein L11P | 431 | 3 | 1 | 0.06 | 0.04 | non-functional |
| CSYN00684 | anti-sigma factor, ChrR-family | 638 | 11 | 5 | 0.15 | 0.14 | non-functional |

Segment-7b contains a set of 13 recoded genes that are essential or of high-fitness cost for standard growth in PYE media. 3 synthetic parts out of 13 (23.1%) fail functionality test by synthetic complementation analysis. Proper part functioning is verified for the remaining 11 genes representing 76.9% of the synthetic parts located on segment-7b. A total of 255,294 transposon insertions were mapped for the test strain segment-7b.

TABLE 3

Segment 8

| Name | Product | [bp] | Tn5 Hits CON | Tn5 Hits TEST | Fitness Value CON | Fitness Value TEST | FUNCT |
|---|---|---|---|---|---|---|---|
| CSYN00690 | CarD-family transcriptional regulator | 503 | 2 | 15 | 0.03 | 0.84 | functional |
| CSYN00691 | ferredoxin | 341 | 3 | 13 | 0.08 | 1.08 | functional |
| CSYN00699 | LSU ribosomal protein L28P | 299 | 6 | 17 | 0.17 | 1.6 | functional |
| CSYN00708 | cobaltochelatase cobT subunit | 1928 | 16 | 96 | 0.07 | 1.4 | functional |
| CSYN03931 | hypothetical protein | 293 | 2 | 2 | 0.06 | 0.19 | functional |
| CSYN00721 | chaperonin GroEL | 1643 | 2 | 43 | 0.01 | 0.74 | functional |
| CSYN00722 | chaperonin GroES | 290 | 3 | 12 | 0.09 | 1.17 | functional |
| CSYN00735 | beta-barrel assembly machine (BAM) protein BamF | 569 | 21 | 15 | 0.32 | 0.74 | functional |
| CSYN00736 | lipoprotein signal peptidase | 506 | 13 | 22 | 0.22 | 1.23 | functional |
| CSYN00737 | isoleucyl-tRNA synthetase | 2909 | 9 | 140 | 0.03 | 1.36 | functional |
| CSYN03934 | hypothetical protein | 44 | 4 | 0 | 0.79 | 0 | non-functional |

TABLE 3-continued

| | | | Tn5 Hits | | Fitness Value | | |
|---|---|---|---|---|---|---|---|
| Name | Product | [bp] | CON | TEST | CON | TEST | FUNCT |
| CSYN00740 | riboflavin kinase/FMN adenylyltransferase | 941 | 7 | 6 | 0.06 | 0.18 | functional |
| CSYN00748 | ferrous iron transport protein A | 320 | 5 | 2 | 0.14 | 0.18 | non-functional |
| CSYN00749 | ferrous iron transport protein B | 1895 | 4 | 8 | 0.02 | 0.12 | non-functional |
| CSYN00758 | translation elongation factor P EF-P | 566 | 2 | 4 | 0.03 | 0.2 | functional |
| CSYN00761 | conserved hypothetical protein | 209 | 4 | 19 | 0.17 | 2.57 | functional |
| CSYN00763 | electron transfer flavoprotein alpha subunit | 941 | 6 | 1 | 0.06 | 0.03 | non-functional |
| CSYN00764 | electron transfer flavoprotein beta subunit | 746 | 3 | 2 | 0.03 | 0.08 | non-functional |
| CSYN00779 | TonB superfamily protein | 401 | 35 | 21 | 0.76 | 1.48 | functional |

Segment-8 contains a set of 19 recoded genes that are essential or of high-fitness cost for standard growth in PYE media. 5 synthetic parts out of 18 (27.8%) fail functionality test by synthetic complementation analysis. Proper part functioning is verified for the remaining 11 genes representing 72.2% of the synthetic parts located on segment-8. A total of 206,858 transposon insertions were mapped for the test strain segment-8.

TABLE 4

Segment 9

| | | Tn5 Hits | | Fitness Value | | |
|---|---|---|---|---|---|---|
| Name | Product | CON | TEST | CON | TEST | FUNCT |
| CSYN00805 | GTP-binding protein YihA | 689 | 5 | 42 | 0.06 | 0.95 functional |
| CSYN00806 | inner membrane protein translocase component yidC | 1847 | 5 | 123 | 0.02 | 1.03 functional |
| CSYN00807 | ribonuclease P protein component | 449 | 6 | 18 | 0.12 | 0.62 functional |
| CSYN00808 | LSU ribosomal protein L34P | 134 | 0 | 0 | 0 | 0 non-funct. |
| CSYN00845 | antitoxin protein relB-1 | 263 | 16 | 21 | 0.53 | 1.24 functional |
| CSYN03943 | hypothetical protein | 161 | 0 | 0 | 0 | 0 non-functional |
| CSYN00860 | holdfast inhibitor protein HfiA | 236 | 14 | 17 | 0.52 | 1.12 functional |
| CSYN00862 | xylonate dehydratase xylD | 1775 | 8 | 1 | 0.04 | 0.01 non-funct. |
| CSYN00874 | biotin synthesis protein bioC | 911 | 11 | 58 | 0.11 | 0.99 functional |
| CSYN00878 | ATP-dependent RNA helicase | 1430 | 33 | 83 | 0.20 | 0.90 functional |
| CSYN00883 | 3-demehylubiquinone 3-methyltransferase | 758 | 10 | 66 | 0.11 | 1.35 functional |
| CSYN00886 | aspartokin | 1247 | 4 | 141 | 0.03 | 1.75 functional |
| CSYN00892 | phosphoenolpyruvate-prot phosphotransferase | 2264 | 48 | 215 | 0.18 | 1.47 functional |
| CSYN00893 | HTH DNA-binding protein | 1064 | 2 | 81 | 0.02 | 1.18 functional |
| CSYN00894 | 1-hydroxy-2-methyl-2-(E)-butenyl 4-diphosphate synthase | 1151 | 5 | 82 | 0.04 | 1.10 functional |
| CSYN00895 | conserved hypothetical protein | 275 | 26 | 7 | 0.82 | 0.39 non-funct. |
| CSYN00896 | conserved hypothetical protein | 371 | 12 | 11 | 0.28 | 0.46 functional |
| CSYN00899 | bacterial peptide chain Release factor 1 | 1070 | 14 | 102 | 0.11 | 1.48 functional |
| CSYN00919 | hypothetical protein | 224 | 5 | 4 | 0.19 | 0.28 functional |
| CSYN00920 | conserved hypothetical protein | 1112 | 39 | 18 | 0.31 | 0.25 non-funct. |

Segment-9 contains a set of 20 recoded genes that are essential or of high-fitness cost for standard growth in PYE media. 5 synthetic parts out of 20 (25.0%) fail functionality test by synthetic complementation analysis. Proper part functioning is verified for the remaining 15 genes representing 75.0% of the synthetic parts located on segment-9. A total of 329,946 transposon insertions were mapped for the test strain segment-9.

TABLE 5

Segment 10

| Name | Product | [bp] | Tn5 Hits CON | Tn5 Hits TEST | Fitness Value CON | Fitness Value TEST | FUNCT |
|---|---|---|---|---|---|---|---|
| CSYN00941 | tRNA methyltransferase MnmA | 1223 | 8 | 80 | 0.06 | 0.91 | functional |
| CSYN00944 | flagellar hook length determination protein | 1202 | 32 | 28 | 0.23 | 0.32 | functional |
| CSYN00948 | CtrA inhibitory protein SciP | 281 | 2 | 11 | 0.06 | 0.55 | functional |
| CSYN00966 | pyridoxamine 5-phosphate oxidase | 668 | 7 | 39 | 0.09 | 0.81 | functional |
| CSYN00976 | signal peptide peptidase A | 1784 | 5 | 149 | 0.02 | 1.17 | functional |
| CSYN01001 | ribokinase | 911 | 3 | 60 | 0.03 | 0.92 | functional |
| CSYN01003 | flagellar biosynthesis protein FliO | 320 | 25 | 40 | 0.68 | 1.74 | functional |
| CSYN01060 | type I protein secretion RsaD | 1736 | 74 | 79 | 0.37 | 0.63 | functional |
| CSYN01095 | phenylalanyl-tRNA synthetase beta chain | 2399 | 15 | 182 | 0.05 | 1.06 | functional |
| CSYN01096 | phenylalanyl-tRNA synthetase alpha chain | 1073 | 9 | 101 | 0.07 | 1.31 | functional |
| CSYN01097 | LSU ribosomal protein L20P | 356 | 7 | 24 | 0.17 | 0.94 | functional |
| CSYN01098 | LSU ribosomal protein L35P | 200 | 6 | 12 | 0.26 | 0.84 | functional |
| CSYN01101 | translation initiation factor 3 (IF-3) | 521 | 3 | 47 | 0.05 | 1.26 | functional |
| CSYN01103 | ADP-heptose--LPS heptosyltransferase | 971 | 2 | 89 | 0.02 | 1.28 | functional |
| CSYN01104 | glycosyltransferase | 1172 | 5 | 84 | 0.04 | 1 | functional |
| CSYN01114 | cysteine desulfurase subunit SufE | 425 | 7 | 25 | 0.14 | 0.82 | functional |

The synthetic segment-10 contains a set of 16 recoded genes including 16 CDS that are essential or of high-fitness cost for standard growth in PYE media. Proper part functioning is verified for all 16 genes representing 100.0% of the synthetic parts located on segment-10. A total of 294,405,562 transposon insertions were mapped for the test strain segment-10.

TABLE 6

Segment 11

| Name | Product | [bp] | Tn5 Hits CON | Tn5 Hits TEST | Fitness Value CON | Fitness Value TEST | FUNCT |
|---|---|---|---|---|---|---|---|
| CSYN01116 | histidine protein kinase DivJ | 1757 | 12 | 10 | 0.06 | 0.12 | non-funct. |
| CSYN01118 | conserved hypothetical protein | 329 | 5 | 6 | 0.13 | 0.38 | functional |
| CSYN01132 | sensory transduction histidine kinase/receiver protein CckA | 2075 | 4 | 41 | 0.02 | 0.41 | functional |
| CSYN01210 | nucleotidyltransferase family protein | 761 | 26 | 2 | 0.3 | 0.05 | non-funct. |
| CSYN01211 | MobA-like NTP transferase domain protein | 875 | 8 | 39 | 0.08 | 0.92 | functional |
| CSYN01212 | dATP pyrophosphohydrolase | 1154 | 31 | 83 | 0.23 | 1.49 | functional |
| CSYN01213 | YjgP/YjgQ family membrane permease | 1061 | 22 | 46 | 0.18 | 0.9 | functional |
| CSYN01214 | YjgP/YjgQ family membrane permease | 1220 | 21 | 29 | 0.15 | 0.49 | functional |

TABLE 6-continued

Segment 11

| Name | Product | [bp] | Tn5 Hits | | Fitness Value | | FUNCT |
|---|---|---|---|---|---|---|---|
| | | | CON | TEST | CON | TEST | |
| CSYN01215 | histidine triad (HIT) hydrolase | 437 | 40 | 37 | 0.8 | 1.75 | functional |
| CSYN01217 | phosphatidylglycerophosphate synthase | 1127 | 50 | 89 | 0.39 | 1.64 | functional |
| CSYN01218 | sphingosine kinase/diacylglycerol kinase-related protein | 992 | 29 | 46 | 0.25 | 0.96 | functional |
| CSYN01219 | putative cytosolic protein | 881 | 17 | 50 | 0.17 | 1.18 | functional |
| CSYN01220 | 7-keto-8-aminopelargonate synthetase | 1214 | 41 | 116 | 0.29 | 1.98 | functional |
| CSYN01221 | acyl carrier protein | 260 | 15 | 21 | 0.5 | 1.67 | functional |
| CSYN01222 | NADH-ubiquinone oxidoreductase | 953 | 20 | 6 | 0.18 | 0.13 | non-funct. |
| CSYN01223 | acyl-CoA synthetase | 1718 | 33 | 124 | 0.17 | 1.49 | functional |
| CSYN01224 | O-antigen membrane transport protein | 1331 | 19 | 17 | 0.12 | 0.26 | functional |
| CSYN01225 | glycerophosphotransferase-related protein | 220 | 8 | 5 | 0.32 | 0.47 | functional |
| CSYN01226 | conserved hypothetical protein | 632 | 15 | 45 | 0.21 | 1.47 | functional |

Segment-11 contains a set of 19 recoded genes that are essential or of high-fitness cost for standard growth in PYE media. 3 synthetic parts out of 19 (15.8%) fail functionality test by synthetic complementation analysis. Proper part functioning is verified for the remaining 16 genes representing 84.2% of the synthetic parts located on segment-11. A total of 329,946 transposon insertions were mapped for the test strain.

TABLE 7

Segment 29

| Name | Product | [bp] | Tn5 Hits | | Fitness Value | | FUNCT |
|---|---|---|---|---|---|---|---|
| | | | CON | TEST | CON | TEST | |
| CSYN_R0061* | RNase P RNA | 399 | 3 | 3 | 0.06 | 0.04 | non-funct. |
| CSYN_02650 | N-acetyl-anhydromuramyl-L-Ala amidase | 728 | 9 | 96 | 0.11 | 0.95 | functional |
| CSYN_02678 | conserved transmembrane protein | 884 | 12 | 133 | 0.12 | 1.08 | functional |
| CSYN_02679 | conserved transmembrane protein | 752 | 16 | 115 | 0.19 | 1.10 | functional |
| CSYN_02695 | hypothetical protein | 218 | 10 | 33 | 0.41 | 1.09 | functional |
| CSYN_02698 | Inosine-uridine nucleoside N-ribohydrolase | 971 | 13 | 132 | 0.12 | 0.97 | functional |
| CSYN_02704* | NADP-dependent malic enzyme | 2276 | 2 | 270 | 0.01 | 0.85 | functional |
| CSYN_02705* | cold shock protein CspC | 209 | 1 | 19 | 0.04 | 0.65 | functional |
| CSYN_02719 | hypothetical protein | 614 | 24 | 47 | 0.35 | 0.55 | functional |
| CSYN_02721 | peptidase, M16 family | 2930 | 107 | 324 | 0.32 | 0.79 | functional |
| CSYN_R0071* | tRNA-Leu | 84 | 0 | 3 | 0.00 | 0.21 | functional |
| CSYN_02759* | methionine aminopeptidase | 830 | 9 | 168 | 0.10 | 1.45 | functional |
| CSYN_02789 | Xre-family transcriptional regulator | 209 | 6 | 13 | 0.26 | 0.45 | functional |
| CSYN_02804 | hypothetical protein | 200 | 4 | 38 | 0.18 | 1.36 | functional |
| CSYN_02818 | hypothetical protein | 113 | 2 | 4 | 0.16 | 0.25 | non-funct. |
| CSYN_02835 | CpxP-related protein | 629 | 20 | 43 | 0.28 | 0.49 | functional |
| CSYN_02836 | conserved hypothetical protein | 452 | 10 | 30 | 0.20 | 0.48 | functional |
| CSYN_02841* | hypothetical protein | 239 | 5 | 4 | 0.19 | 0.12 | non-funct. |
| CSYN_02844* | antitoxin protein parD-3 | 218 | 9 | 27 | 0.37 | 0.89 | functional |
| CSYN_02855 | PepSY peptidase propeptide domain | 317 | 7 | 25 | 0.20 | 0.57 | functional |
| CSYN_02866 | conserved membrane protein | 464 | 14 | 57 | 0.27 | 0.88 | functional |
| CSYN_02869* | conserved hypothetical protein | 284 | 9 | 6 | 0.28 | 0.15 | non-funct. |
| CSYN_02934 | conserved hypothetical protein | 701 | 11 | 47 | 0.14 | 0.48 | functional |

Segment-29 contains a set of 23 recoded genes including RNase P RNA, tRNA-Leu and 21 CDS that are essential or of high-fitness cost for standard growth in PYE media. Four synthetic parts out of 23 (17.4%) fail functionality test by synthetic complementation analysis. Proper part functioning is verified for the remaining 19 genes representing 82.6% of the synthetic parts located on segment-29. For the control strain, a total of 464,607 transposon insertions were mapped, for the test strain 527,275 chromosomal and 8,400 insertions within the synthetic plasmid pMR10_segment-29 were mapped.

TABLE 8

Segment 30

| Name | Product | [bp] | Tn5 Hits CON | Tn5 Hits TEST | Fitness Value CON | Fitness Value TEST | FUNCT |
|---|---|---|---|---|---|---|---|
| CSYN02941 | transcription elongation factor greA | 473 | 38 | 3 | 0.7 | 0.08 | non-functional |
| CSYN02942 | nucleoside-diphosphate-sugar epimerase | 1169 | 15 | 102 | 0.11 | 1.17 | functional |
| CSYN02957 | ArsR-family transcriptional regulator | 362 | 23 | 45 | 0.55 | 1.66 | functional |
| CSYN02964 | thioredoxin-disulfide reductase | 1007 | 10 | 109 | 0.09 | 1.45 | functional |
| CSYN02975 | excinuclease ABC subunit C | 1922 | 52 | 192 | 0.24 | 1.34 | functional |
| CSYN03002 | CDP-diacylglycerol--glycerol-3-phosphate3-phosphatidyltransferase | 617 | 12 | 53 | 0.17 | 1.15 | functional |
| CSYN03006 | quinolinate synthetase A | 1103 | 7 | 74 | 0.06 | 0.9 | functional |
| CSYN03007 | L-aspartate oxidase | 1535 | 22 | 51 | 0.12 | 0.44 | functional |
| CSYN03009 | nicotinate-nucleotide pyrophosphorylase | 848 | 3 | 55 | 0.03 | 0.87 | functional |
| CSYN03026 | two-component response regulator petR | 701 | 3 | 43 | 0.04 | 0.82 | functional |
| CSYN03029 | 3-deoxy-manno-octulosonate cytidylyltransferase | 737 | 4 | 1 | 0.05 | 0.02 | non-functional |
| CSYN03031 | NlpC/P60 family protein | 839 | 29 | 33 | 0.3 | 0.53 | functional |
| CSYN03052 | acyltransferase | 1172 | 8 | 45 | 0.06 | 0.51 | functional |
| CSYN03073 | hypothetical protein | 524 | 23 | 8 | 0.38 | 0.2 | non-functional |
| CSYN03080 | antitoxin protein parD-4 | 251 | 7 | 28 | 0.24 | 1.49 | functional |
| CSYN03090 | acetyl-coenzyme A carboxylase carboxyl transferase subunit alpha | 962 | 3 | 56 | 0.03 | 0.78 | functional |
| CSYN03103 | shikimate kinase | 602 | 4 | 34 | 0.06 | 0.76 | functional |
| CSYN03104 | 3-dehydroquinate synthase | 1112 | 3 | 85 | 0.02 | 1.02 | functional |

Segment-30 contains a set of 18 recoded genes that are essential or of high-fitness cost for standard growth in PYE media. 3 synthetic parts out of 18 (16.6%) fail functionality test by synthetic complementation analysis. Proper part functioning is verified for the remaining 15 genes representing 83.3% of the synthetic parts located on segment-30. A total of 291,733 transposon insertions were mapped for the test strain.

TABLE 9

Segment 31

| Name | Product | [bp] | Tn5 Hits CON | Tn5 Hits TEST | Fitness Value CON | Fitness Value TEST | FUNCT |
|---|---|---|---|---|---|---|---|
| CSYN03115 | cobaltochelatase cobS subunit | 1010 | 9 | 5 | 0.08 | 0.22 | non-functional |
| CSYN03130 | cell cycle response regulator ctrA | 695 | 1 | 2 | 0.01 | 0.13 | non-functional |
| CSYN03142 | RNA polymerase sigma factor rpoD | 1958 | 4 | 4 | 0.02 | 0.09 | non-functional. |

TABLE 9-continued

Segment 31

| Name | Product | [bp] | Tn5 Hits CON | Tn5 Hits TEST | Fitness Value CON | Fitness Value TEST | FUNCT |
|---|---|---|---|---|---|---|---|
| CSYN03144 | DNA primase | 1931 | 12 | 5 | 0.05 | 0.11 | non-functional |
| CSYN03162 | bifunctional ornithine acetyltransferase/N-acetylglutamate synthase | 1445 | 11 | 5 | 0.07 | 0.15 | non-functional. |
| CSYN03164 | protein translocase subunit secA | 2771 | 26 | 22 | 0.08 | 0.35 | non-functional |
| CSYN03987 | hypothetical protein | 104 | 11 | 5 | 0.92 | 2.1 | functional |
| CSYN03195 | RNA polymerase sigma factor RpoH | 896 | 2 | 3 | 0.02 | 0.15 | non-funct. |
| CSYN03213 | polyhydroxyalkanoic acid system protein | 308 | 10 | 11 | 0.28 | 1.56 | functional |
| CSYN03256 | chorismate synthase | 1118 | 3 | 81 | 0.02 | 3.16 | functional |
| CSYN03274 | hypothetical protein | 116 | 7 | 0 | 0.53 | 0 | non-functional. |
| CSYN03277 | glycosyltransferase | 1049 | 7 | 95 | 0.06 | 3.95 | functional |
| CSYN03304 | translation elongation factor G (EF-G) | 2078 | 5 | 2 | 0.02 | 0.04 | non-functional. |
| CSYN03305 | SSU ribosomal protein S7P | 473 | 0 | 1 | 0 | 0.09 | non-functional. |
| CSYN03306 | SSU ribosomal protein S12P | 371 | 0 | 0 | 0 | 0 | non-functional. |
| CSYN03307 | hypothetical protein | 266 | 3 | 3 | 0.1 | 0.49 | functional |

Segment-31 contains a set of 16 CDS that are essential or of high-fitness cost for standard growth in PYE media. 11 synthetic parts out of 16 (69%) fail functionality test by synthetic complementation analysis. Proper part functioning is verified for the remaining 5 genes representing 31% of the synthetic parts located on segment-31. A total of 308,562 transposon insertions were mapped for the test strain.

The invention claimed is:

1. A method for determining the functionality of a plurality of artificial genetic elements wherein the method comprises the steps of
   a) providing a first plurality of haploid cells comprising a plurality of native genetic elements essential to propagation of said cells;
   b) transforming into the plurality of cells a plurality of artificial genetic elements expected or designed to serve the same biological function as said native genetic elements;
   c) mutagenizing the plurality of cells by high frequency transposon mutagenesis, wherein a transposable element is inserted into said native genetic elements and/or said artificial genetic elements to form a plurality of mutagenized cells;
   d) growing the plurality of mutagenized cells under selective conditions; and thereafter
   e) sequencing the insertion sites of the transposable element in DNA isolated from the plurality of mutagenized cells, thereby determining the insertion frequency of the transposable element in the native and artificial genetic elements, wherein an equal frequency of transposable element insertion in a native genetic element and an artificial genetic element designed to serve the same biological function indicates functionality of an artificial genetic element, and wherein a higher frequency of transposable element insertion in an artificial genetic element than the corresponding native genetic element indicates non-functionality.

2. The method of claim 1, wherein a fraction of said first plurality of cells, serving as control cells, is subjected to said mutagenesis step without first being transformed by the plurality of artificial genetic elements and further comprising sequencing insertion sites of the transposable element in DNA isolated from the control cells thereby determining a frequency of insertion of said transposable element into said native genetic elements of said control cells, and wherein     i. if the frequency of transposon insertion of native genetic element is higher in cells transformed by the plurality of artificial genetic elements than in the control cells, the artificial genetic element designed to serve the same biological function is determined to be functional, and/or     ii. if the frequency of transposon insertion of the native genetic elements are equal in cells transformed by the plurality of artificial genetic elements to the frequency of transposon insertion in the control cells, the artificial element designed to serve the same biological function is determined to be non-functional.

3. The method according to claim 1, wherein said sequencing comprises isolating transposon junction sequences comprising said transposable element and said native genetic elements or said artificial elements by a PCR     with a first primer that anneals to a sequence in said transposable element and a second primer that anneals to a sequence in said native genetic elements, or     with said first primer, a second primer that anneals to a sequence in said native genetic elements and a third primer that anneals both to a sequence in said artificial genetic elements and to a sequence comprised in said native genetic elements.

4. The method according to claim 3, wherein said second primer and/or said third primer is a random primer or a semi-arbitrary primer comprising a 3'penta-nucleotide sequence that is designed to anneal to said native genetic elements or said artificial genetic elements.

5. The method according to claim 1, wherein said transposon mutagenesis is mediated by a genetic construct comprising said transposable element encoding a transposase operable in said cells.

6. The method according to claim 1, wherein said cells are selected from the group consisting of bacteria, archea, and haploid yeast strains.

7. The method according to claim 1, wherein each of said plurality of artificial genetic elements is distinct from any other one of said plurality of artificial genetic elements and serves a different function, and said plurality of cells comprise a plurality of native genetic elements corresponding in function to said plurality of artificial genetic elements.

8. The method according to claim 7, wherein the nucleic acid molecule is a plasmid or an artificial chromosome.

9. The method according to claim 1, wherein more than 1.000 insertion sites are sequenced.

10. The method according to claim 1, wherein said artificial genetic elements are selected from the group consisting of a promoter, an operator, a transcriptional control element, a ribosomal binding site, a translational regulatory sequence, an open reading frame, an operon, a tRNA, a ribosomal RNA gene, a RNA gene, and a transcription terminator.

11. The method of claim 1, wherein if the artificial genetic elements are determined to be functional, the artificial elements are used to comprise a synthetic gene circuit, pathway, chromosome, and/or genome.

\* \* \* \* \*